US011441158B1

(12) United States Patent
Brown et al.

(10) Patent No.: US 11,441,158 B1
(45) Date of Patent: Sep. 13, 2022

(54) TRANSGENIC RESISTANCE TO COTTON LEAF CURL DISEASE USING SMALL HAIRPIN RNA TO INDUCE RNA INTERFERENCE

(71) Applicant: Arizona Board of Regents on Behalf of the University of Arizona, Tucson, AZ (US)

(72) Inventors: Judith K. Brown, Tucson, AZ (US); Muhammad Zia-Ur-Rehman, Lahore (PK)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 20 days.

(21) Appl. No.: 16/370,544

(22) Filed: Mar. 29, 2019

Related U.S. Application Data

(60) Provisional application No. 62/650,211, filed on Mar. 29, 2018.

(51) Int. Cl.
  *C12N 15/82* (2006.01)
  *C12N 5/04* (2006.01)
  *C12N 15/113* (2010.01)

(52) U.S. Cl.
  CPC ........... *C12N 15/8283* (2013.01); *C12N 5/04* (2013.01); *C12N 15/113* (2013.01); *C12N 15/8201* (2013.01); *C12N 2310/122* (2013.01)

(58) Field of Classification Search
  None
  See application file for complete search history.

(56) References Cited

U.S. PATENT DOCUMENTS

2017/0016021 A1* 1/2017 Yeh .................... C12N 15/8283

OTHER PUBLICATIONS

Briddon, R.W.; Markham, P., "Cotton leaf curl virus disease". Virus Res. 2000, 71, 151-159.
Farooq, A.; Farooq, J.; Mahmood, A.; Batool, A.; Rehman, A.; Shakeel, A.; Mehboob, S., "An overview of cotton leaf curl virus disease (CLCuD) a serious threat to cotton productivity." Aust. J. Crop Sci. 2011, 5, 1823-1831.
Farooq, J.; Farooq, A.; Riaz, M.; Shahid, M.R.; Saeed, F.; Iqbal, M.S.; Hussain, T.; Batool, A.; Mahmood, A., "Cotton leaf curl virus disease a principle cause of decline in cotton productivity in Pakistan (a mini review)." Can. J. Plant Prot. 2014, 2, 9-16.
Ali, A.; Abdulai, A., "The adoption of genetically modified cotton and poverty reduction in Pakistan." J. Agric. Econ. 2010, 61, 175-192.
Kerschen, A.; Napoli, C.A.; Jorgensen, R.A.; Müller, A.E., "Effectiveness of RNA interference in transgenic plants." FEBS Lett. 2004, 566, 223-228.
Kirthi, N.; Savithri, H.S., "A conserved zinc finger motif in the coat protein of Tomato leaf curl Bangalore virus is responsible for binding to ssDNA." Arch. Virol. 2003, 148, 2369-2380.
Klahre, U.; Crete, P.; Leuenberger, S.A.; Iglesias, V.A.; Meins, F., "High molecular weight RNAs and small interfering RNAs induce systemic posttranscriptional gene silencing in plants." Proc. Natl. Acad. Sci. USA 2002, 99, 11981-11986, doi:10.1073/pnas. 182204199.
Hannon, G.J., "RNA interference." Nature 2002, 418, 244-251.
Aragão, F.J.; Faria, J.C., "First transgenic geminivirus-resistant plant in the field." Nat. Biotechnol. 2009, 27, 1086-1088.
Asad, S.; Haris, W.A.; Bashir, A.; Zafar, Y.; Malik, K.A.; Malik, N.N.; Lichtenstein, C.P., "Transgenic tobacco expressing geminiviral RNAs are resistant to the serious viral pathogen causing cotton leaf curl disease." Arch. Virol. 2003, 148, 2341-2352.
Baulcombe, D., "RNA silencing." Trends Biochem. Sci. 2005, 30, 290-293.
Shepherd, D.N.; Martin, D.P.; Thomson, J.A., "Transgenic strategies for developing crops resistant to geminiviruses." Plant Sci. 2009, 176, 1-11.
Sohrab, S.S.; Kamal, M.A.; Ilah, A.; Husen, A.; Bhattacharya, P.S.; Rana, D., "Development of Cotton leaf curl virus resistant transgenic cotton using antisense βC1 gene." Saudi J. Biol. Sci. 2014, 23, 358-362.
Muzaffar, A.; Kiani, S.; Khan, M.A.; Rao, A.Q.; Ali, A.; Awan, M.F.; Iqbal, A.; Nasir, I.A.; Shahid, A.A.; Husnain, T., "Chloroplast localization of Cry1Ac and Cry2A protein—an alternative way of insect control in cotton." Biol. Res. 2015, 48, 14.
Malik, H.J.; Raza; A; Amin, I.; Scheffler, J.A.; Scheffler, B.E.; Brown, J.K.; Mansoor, S., "RNAi-mediated mortality of the whitefly through transgenic expression of double stranded RNA homologous to acetylcholinesterase and ecdysone receptor in tobacco plants." Sci. Rep. 2016, 6, 38469.

(Continued)

*Primary Examiner* — Elizabeth F McElwain
(74) *Attorney, Agent, or Firm* — Casimir Jones, S.C.; J. Mitchell Jones

(57) ABSTRACT

The present invention relates to the control of pest infestation by inhibiting or reducing the expression of certain genes implicated in cotton leaf curl virus disease (CLCuD), by simultaneously targeting viral RNA involved in viral replication and movement. More specifically, the invention relates to a method for substantially simultaneously targeting the AC1 gene of a begomovirus and (2) the betasatellite and non-coding region. Strategies using small hairpin RNA (shRNA) constructs are described herein to achieve viral-mediated gene silencing, and an exemplary embodiment is disclosed, for targeting the replication-associated protein gene (AC1) and non-coding region found in numerous species and strains of the cotton leaf curl disease begomovirus complex, and a coding and adjacent non-coding region of the associated betasatellites. The constructs of the invention reduce or prevent replication of the disease-associated virus, and reduce or prevent the ability of a virus to suppress the defenses of the host plant. In an embodiment of the invention, a small interfering RNA construct referred to herein as an shRNA is disclosed. Also disclosed are transgenic cotton plants that are resistant to leaf curl virus disease.

4 Claims, 6 Drawing Sheets
(6 of 6 Drawing Sheet(s) Filed in Color)
Specification includes a Sequence Listing.

(56) References Cited

OTHER PUBLICATIONS

Vyas, M.; Raza, A.; Ali, A.M.; Ashraf, M.A.; Mansoor, S.; Ahmad, A.S.; Brown, J.K., "Knock down of whitefly gut gene expression and mortality by orally delivered gut gene-specific dsRNA." PLoS ONE 2017, 12, e0168921, doi:10.1371/journal.pone.016892.
Amin, I.; Hussain, K.; Akbergenov, R.; Yadav, J.S.; Qazi, J.; Mansoor, S.; Briddon, R.W., "Suppressors of RNA silencing encoded by the components of the Cotton leaf curl begomovirus-betasatellite complex." Mol. Plant Microbe Interact. 2011, 24, 973-983.
Briddon, R.W.; Stanley, J., "Subviral agents associated with plant single-stranded DNA viruses." Virology 2006, 344, 198-210.
Cui, X.; Li, G.; Wang, D.; Hu, D.; Zhou, X., "A begomovirus DNAβ-encoded protein binds DNA, functions as a suppressor of RNA silencing, and targets the cell nucleus." J. Virol. 2005, 79, 10764-10775.
Kong, L.J.; Orozco, B.M.; Roe, J.L.; Nagar, S.; Ou, S.; Feiler, H.S.; Hanley-Bowdoin, L., "A geminivirus replication protein interacts with the retinoblastoma protein through a novel domain to determine symptoms and tissue specificity of infection in plants." J. EMBO. 2000, 19, 3485-3495.
Laufs, J.; Schumacher, S.; Geisler, N.; Jupin, I.; Gronenborn, B., "Identification of the nicking tyrosine of geminivirus Rep protein." FEBS Lett. 1995, 377, 258-262.
Saeed, M.; Behjatnia, S.A.; Mansoor, S.; Zafar, Y.; Hasnain, S.; Rezaian, M.A., "A single complementary-sense transcript of a geminiviral DNA β satellite is determinant of pathogenicity." Mol. Plant Microbe Interact. 2005, 18, 7-14.
Saeed, M.; Zafar, Y.; Randles J, W.; Rezaian, M.A., "A monopartite begomovirus-associated DNA β satellite substitutes for the DNA B of a bipartite begomovirus to permit systemic infection." J. Gen. Virol. 2007, 88, 2881-2889.
Napoli, C.; Lemieux, C.; Jorgensen, R., "Introduction of a chimeric chalcone synthase gene into petunia results in reversible co-suppression of homologous genes in trans." Plant Cell 1900, 2, 279-289.
Rao, A.Q.; Bakhsh, A.; Kiani, S.; Shahzad, K.; Shahid, A.A.; Husnain, T.; Riazuddin, S., "The myth of plant transformation." Biotechnol. Adv. 2009, 27, 753-763.
Doyle, J.J., "A rapid DNA isolation procedure for small quantities of fresh leaf tissue." Phytochem. Bull. 1987, 19, 11-15.
Rao, A.Q.; Irfan, M.; Saleem, Z.; Husnain, T.; Riazuddin, S., "Overexpression of the Phytochrome B Gene of *Arabidopsis thaliana* increases the yield of cotton (*Gossypium hirsutum*)." J. Zhejiang Univ. Sci. B 2011, 12, 326-334.
Akhtar, K.P.; Ullah, R.; Khan, I.A.; Saeed, M.; Sarwar, N.; Mansoor, S., "First symptomatic evidence of infection of Gossypium arboreum with Cotton leaf curl Burewala virus through grafting." Int. J. Agric. Biol. 2013, 15, 157-160.
Rahman, M.; Noreen, S.; Husnain, T.; Riazuddin, S., "A fast and efficient method to determine the position of alien genes in transgenic plants." Emir. J. Food Agric. 2010, 22, 223-231.
Rahman, N.; Khatoon, A.; Rahman, H., "Studies on the development of spectrophotometric method for the determination of haloperidol in pharmaceutical preparations." Quím. Nova 2012, 35, 392-397.
Mathews, D.H.; Turner, D.H.; Watson, R.M., "RNA secondary structure prediction." Curr. Protoc. Nucleic Acid Chem. 2007, Chapter 11, Unit 11.2.
Akhtar, K.P.; Khan, A.I.; Hussain, M.; Khan, M.S.I., "Comparison of resistance levels to Cotton leaf curl virus (CLCuV) among newly developed cotton mutants and commercial cultivars." J. Plant Pathol. 2002, 18, 179-186.
Ammara, U.; Mansoor, S.; Saeed, M.; Amin, I.; Briddon, R.; Al-Sadi, A., "RNA interference-based resistance in transgenic tomato plants against Tomato yellow leaf curl virus-Oman (TYLCV-OM) and its associated betasatellite." J. Virol. 2015, 12, 38.

\* cited by examiner

SEQUENCE LISTING

<160> NUMBER OF SEQ ID NOS: 6

<210> SEQ ID NO 1
<211> LENGTH: 715
<212> TYPE: DNA
<213> ORGANISM: Unknown
<220> FEATURE:
<223> OTHER INFORMATION: Cotton leaf curl Kokhran virus-Burewala

<400> SEQUENCE: 1

```
tctagaccgg tttttgataa aggagtgtat aggtttcacg agagattgat ttcttctccg      60
tgaaagggtt aacgtttggg atctttgggg ctgcttcttc tttaagtagt tctagacatc     120
tctcgaagtg cttctaccca gaggcgtata ggtacaagag taggttaagc ttccctttaa     180
ggtcacgttt ttattgtcta agaagctgaa ccaaaggggt tcagccagtc gtgtaaaggt     240
aggcttgtaa gtcccccgat ttagtcgcag actacagttt ttgatgtagc ggtttctacc     300
tctgcaagaa ttcacatgaa cttttgggtc tctataaccc ttacctacat tagcttggta     360
tgtataagtt attcttcaag tgtcaaattt aaggttggtg ttgggtcatt acgtataaat     420
tgtgtgtata gtggttgttg tttgtctggg tattaggtat ttgccggtag aagtttccgg     480
gttagtgaag gttcaggtaa tttaaccggg taatcttcag tttaggtcag ttctgttcgt     540
caccctgggt gacgcgccgg tagcccgtgg cgagcgggtg ccattataat cttgcacccg     600
ctcgattcga ggccgcatcg attccgacga cgcatcgcat caccaaagat gggagggtcc     660
ccatgtgtgg cggcgcgcat agcatttaac tacggcctta gtcggtcaag gatcc         715
```

<210> SEQ ID NO 2

```
<211> LENGTH: 715
<212> TYPE: DNA
<213> ORGANISM: Unknown
<220> FEATURE:
<223> OTHER INFORMATION: Cotton leaf curl Kokhran virus-Burewala

<400> SEQUENCE: 2
ccatggaact ggctgattcc ggcatcaatt tacgatacgc gcggcggtgt gtacccctgg      60
gagggtagaa accactacgc tacgcagcag ccttagctac gccggagctt agctcgccca     120
cgttctaata ttaccgtggg cgagcggtgc ccgatggccg cgcagtgggt cccactgctt     180
gtcttgactg gatttgactt ctaatgggcc aatttaatgg acttggaagt gattgggcct     240
ttgaagatgg ccgtttatgg attatgggtc tgtttgttgt tggtgatatg tgtgttaaat     300
atgcattact gggttgtggt tggaatttaa actgtgaact tcttattgaa tatgtatggt     360
tcgattacat ccattcccaa tatctctggg ttttcaagta cagaattcaa cgtctccatc     420 tttgcgatg tagtttttga catcagacgc tgatttagcc ccctgaatgt tcggatggaa      480
atgtgctgac cgacttgggg aaaccaagtc gaagaatctg ttatttttgc actggaattt     540
cccttcgaat tggatgagaa catggatatg cggagaccca tcttcgtgaa gctctctaca     600
gatcttgatg aatttcttct tcgtcgggt ttctagggtt tgcaattggg aaagtgcctc      660
ttctttagtt agagagcact ttggatatgt gaggaaatag ttttggccc tcgag           715

<210> SEQ ID NO 3
<211> LENGTH: 23
<212> TYPE: DNA
<213> ORGANISM: Unknown
<220> FEATURE:
<223> OTHER INFORMATION: Cotton leaf curl Kokhran virus-Burewala

<400> SEQUENCE: 3
tgccaaaaac tatttcctca cat                                              23

<210> SEQ ID NO 4
<211> LENGTH: 19
<212> TYPE: DNA
<213> ORGANISM: Unknown
<220> FEATURE:
<223> OTHER INFORMATION: Cotton leaf curl Kokhran virus-Burewala

<400> SEQUENCE: 4
aacgtctcca tctttggcg                                                   19

<210> SEQ ID NO 5
<211> LENGTH: 20
<212> TYPE: DNA
<213> ORGANISM: Unknown
<220> FEATURE:
<223> OTHER INFORMATION: Cotton leaf curl Multan virus

<400> SEQUENCE: 5
agtgcgctga aaaggtgat                                                   20

<210> SEQ ID NO 6
<211> LENGTH: 22
<212> TYPE: DNA
```

```
<213> ORGANISM: Unknown
<220> FEATURE:
<223> OTHER INFORMATION: Cotton leaf curl Multan virus

<400> SEQUENCE: 6
attaaaacgt gaaaaggtg at                                              22
```

TRANSGENIC RESISTANCE TO COTTON LEAF CURL DISEASE USING SMALL HAIRPIN RNA TO INDUCE RNA INTERFERENCE

CROSS-REFERENCE TO RELATED APPLICATIONS

This application claims priority to U.S. Provisional Application No. 62/650,211, filed on Mar. 29, 2018, the entire contents of which are incorporated herein by reference.

GOVERNMENT FUNDING

This invention was made with government support under Grant Nos. 58-6402-2-763 and 58-6402-O-178F awarded by USDA/ARS. The United States government has certain rights in the invention.

SEQUENCE LISTING

The Sequence Listing submitted concurrently with this application as an ASCII text file via EFS-Web is hereby incorporated by reference. The ASCII text file was generated on Mar. 29, 2019 using PatentIn version 3.5, the name of the Sequence Listing is 3_29_2019_Sequence_Listing_037145_0008_ST25.txt, and the size of the ASCII text file is 4 KB.

FIELD OF THE INVENTION

The present invention relates to the field of controlling pests that attack crops, especially cotton plants.

BRIEF SUMMARY OF THE INVENTION

The present invention relates to the control of pest infestation by inhibiting or reducing the expression of certain genes implicated in cotton leaf curl virus disease (CLCuD), by substantially simultaneously targeting viral RNA involved in viral replication and movement. More specifically, the invention relates to a method for substantially simultaneously targeting the AC1 gene of a virus and (2) the βC1 gene and satellite conserved region of a virus. Small hairpin RNA (shRNA) constructs are described herein, and an exemplary embodiment is disclosed, for targeting the replication-associated protein gene (AC1) and non-coding region found in numerous species and strains of the cotton leaf curl disease begomovirus complex, and a coding and adjacent non-coding region of the associated betasatellites. The constructs of the invention reduce or prevent replication of the disease-associated virus, and reduce or prevent the ability of a virus to suppress the defenses of the host plant. The invention further relates to a method for producing transgenic cotton plants that are resistant to several recognized "core" and "non-core" leaf curl virus disease-causing begomoviruses endemic to the Indian Subcontinent. Some of these viruses occur in China, the Philippines, and are considered high risk pathogens to cotton in Australia, South America and the USA.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A illustrates the detection of transgene integration in the $T_0$ generation of transgenic cotton plants by PCR amplification using AC1-specific primers, yielding the expected size ~300 bp amplicon. Lanes 1-5: PCR amplification products from transgenic cotton plants; Lane 6 and 8: positive controls (full-length CLCu-KoV-Bu DNA-A clone); Lane 7: 1 kb ladder; and Lanes 9-12: PCR products amplified from transgenic cotton plants. FIG. 2B illustrates the detection of transgene integration in DNA isolated from $T_1$ generation transgenic cotton plants by PCR using CLCuKoV-Bu AC1-specific primers, which yielded the expected size ~300 bp amplicon, and confirmatory DNA sequencing. Lane 1: 1 kb ladder; Lane 2: positive control, full-length CLCuKoV-Bu DNA-A clone); Lanes 3-9: PCR products amplified from transgenic cotton plants according to an embodiment of the invention.

FIG. 7A shows metastatic data for $T_1$ transgenic cotton plants. The arrow indicates the location of transgene integration, as visualized by hybridization with a sequence-specific probe and fluorescent microscopy. FIG. 7B shows karyotyping of a transgenic cotton plant Vβ6 in the $T_1$ generation. The arrow indicates the location of the transgene on chromosome 6, visualized after chromosomes were re-ordered consecutively, using the karyotyping software Cytovision Genus version 3.93 Applied Imaging USA.

DETAILED DESCRIPTION OF THE INVENTION

Figure 1:
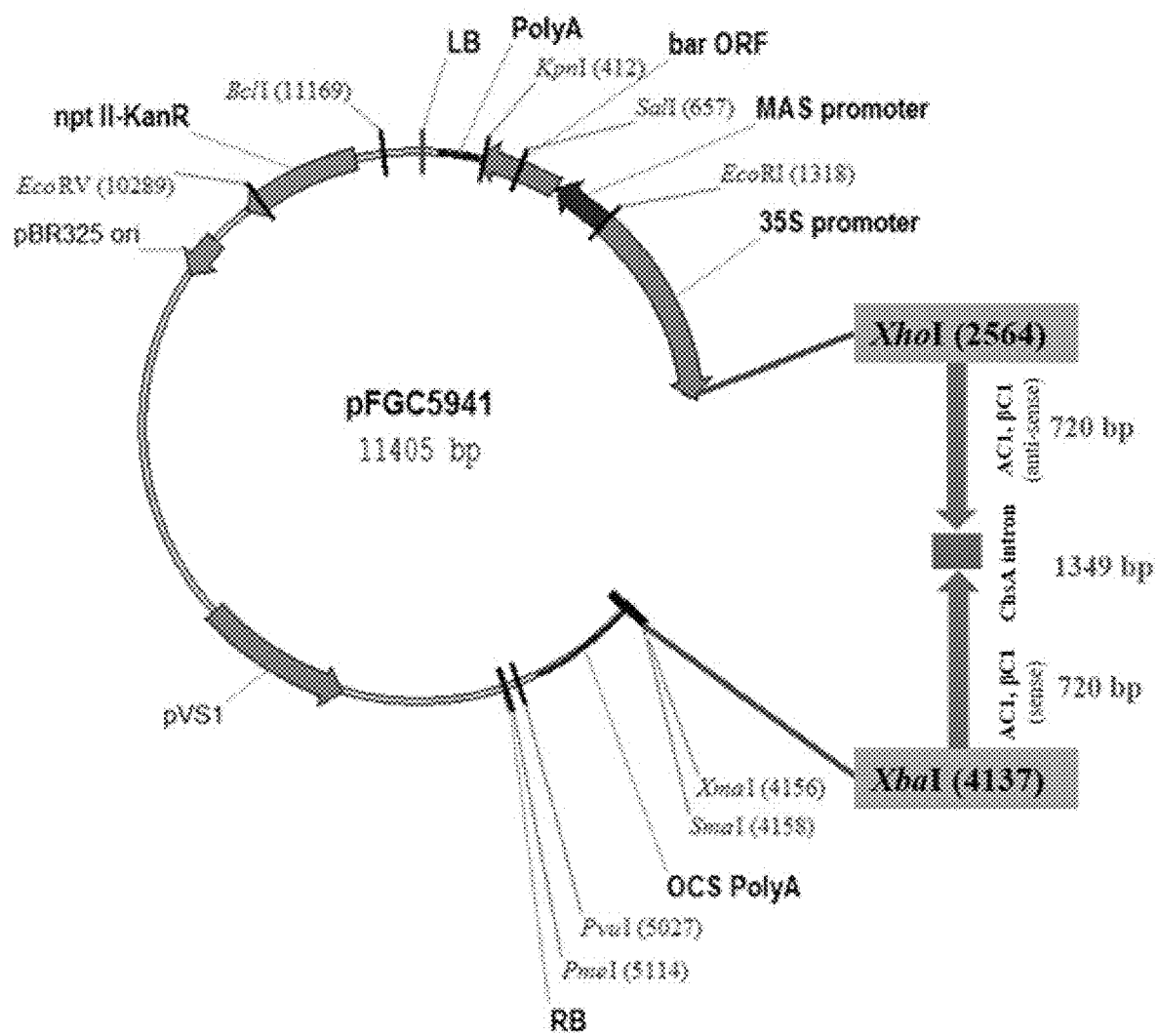
FIG. 1 is a schematic representation of a map of a begomovirus-betasatellite construct, VP, according to an embodiment of the invention.
Figure 2A:
FIGS. 2A and 2B illustrate the results of polymerase chain reaction (PCR) amplification analysis to confirm the transgene presence in $T_0$ and $T_1$.
Figure 2B:
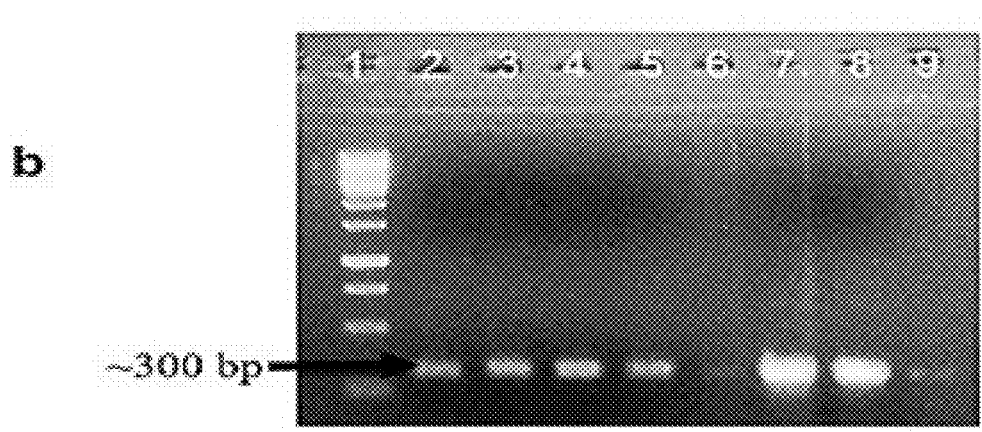

The present invention relates to the control of pest infestation by inhibiting or reducing the expression of certain genes and non-coding regulatory regions implicated in the infection cycle of the begomoviral causal agents of cotton leaf curl virus disease (CLCuD). The invention involves designing and preparing a small hairpin RNA (shRNA) construct which targets viral RNA involved in replication and movement of viruses. A small hairpin RNA (shRNA) construct is disclosed which targets the replication-associated protein gene (AC1) and non-coding region found in numerous species and strains of cotton leaf curl disease begomovirus compels, and a coding and adjacent non-coding region of the associate betasatellites. The invention further relates to methods for producing transgenic cotton plants that are resistant to leaf curl virus disease caused by a large number of species or strains of the endemic leaf curl begomovirus complex in south Asia, and elsewhere, where the virus-betasatellites have been introduced. In one embodiment of the invention, a shRNA construct is disclosed, which targets the AC1 gene of Cotton leaf curl Kokhran virus-Burewada (CLCuKoV-Bu) and the βC1 gene and satellite conserved region of the Cotton leaf curl Multan betasatellite (CLCuMB).

Cotton leaf curl virus disease (CLCuD) is caused by a number of different whitefly-transmitted begomovirus species and strains, resulting in extensive losses annually in India and Pakistan. One embodiment of the present invention involves the design of a synthetic, small interfering RNA, specifically a small hairpin RNA (shRNA) construct which strategically targets the AC1 gene and selected non-coding region of Cotton leaf curl Kokhran virus-Burewala (CLCuKoV-Bu), and the βC1 gene and satellite conserved region of the Cotton leaf curl Multan betasatellite (CLCuMB). The AC1 gene and non-coding region, and the CLCuMB coding and non-coding conserved region function in replication initiation, and suppression of the plant host defense (gene-silencing) pathway, respectively. The construct, Vβ, was transformed into cotton plants using the *Agrobacterium*-mediated embryo shoot apex cut method.

Results from fluorescence in situ hybridization (FISH) and karyotyping assays indicated that six of the eleven (11) $T_1$ plants harbored a single copy of the Vβ transgene. Transgenic cotton plants and non-transgenic (susceptible) test plants included as the positive control were challenge-inoculated using the viruliferous whitefly vector to transmit the CLCuKoV-Bu/CLCuMB complex. Among the test plants, plant Vβ-6 was asymptomatic, had the lowest amount of detectable virus, and harbored a single copy of the transgene on chromosome six. Absence of characteristic leaf curl symptom development in transgenic Vβ-6 cotton plants, and significantly reduced begomoviral-betasatellite accumulation based on real-time PCR, indicated the successful knockdown of CLCuKoV-Bu and CLCuMB expression, resulting in leaf curl resistant plants.

Cotton leaf curl disease (CLCuD) is caused by a number of different begomoviral species and strains that infect a wide range of plant genera, including cotton, *Gossypium* spp., many of which are members of the Malvaceae. In Pakistan, crop losses due to leaf curl disease have ranged between 5% and 30% or more since 1990, having an estimated worth of US$5 billion. During the 2008-2009 outbreak, losses amounted to ~1.12 million bales, affecting over 1.48 million hectares [1,2,3].

Despite the widespread use of transgenic solutions to pest control in cotton—for example, Bt-toxin expression to reduce feeding damage by lepidopteran pests—and the robust evidence showing that pathogen-derived resistance based on gene silencing is effective for combatting diseases caused by plant viruses [5-7], the commercialization of transgenic technology for virus disease control has been limited [3]. In particular, RNA-interference (RNAi) [8], induced by double-stranded (ds) RNA, has been shown to be highly effective for silencing viral gene expression in plants to achieve disease resistance, including for geminiviruses [9-13]. Stable knockdown of viral gene expression has been demonstrated using small interfering RNA (siRNA) technology by targeting viral coding and non-coding regions involved in viral replication and movement, which are crucial for establishing system infection of the host plant [8,11]. The knockdown effect of RNAi spreads systemically throughout the plant, insects, and in certain other organisms harboring RNAi machinery, the dsRNA is exported to neighboring cells [7]. The present invention, which uses RNAi technology, could help alleviate the overwhelming reliance on chemical pesticides for controlling insect vectors [14], such as the whitefly, *Bemisia tabaci* (Genn.), which transmits begomoviruses [15,16], while also reducing rates of virus transmission.

Begomoviruses (family, Geminiviridae; genus, Begomovirus) are small, single-stranded DNA viruses that are pathogens of cultivated and non-cultivated wild plant species, nearly worldwide. They have either a bipartite (DNA-A and DNA-B) or monopartite (DNA-A) genome organization. Many monopartite begomoviruses require an associated betasatellite to facilitate systemic infection of the plant host, in part by suppressing plant host defenses [17-19]. The begomoviral AC1 gene, or replication (Rep)-associated protein, encoded on all DNA-A components, is a multifunctional protein that localizes to the plant nucleus. The AC1 is essential for regulating begomoviral transcription and replication of viral DNA [20,21] following the introduction of a nick at the origin of replication (ori). The Rep-associated protein also interacts with sequences in the satellite-conserved region (SCR) of the betasatellite, or DNA β-satellite [20] to facilitate its replication. The DNA β-satellite SCR shares an identical nonanucleotide sequence with its respective "helper virus", suggesting this non-coding region is essential for β-satellite replication initiation. The SCR and its position in the DNA β-satellite molecule appears to be analogous to the common region position of bipartite begomoviruses [18].

Begomovirus-associated β-satellites modulate begomovirus virulence, and therefore infection and systemic spread, thereby directly influencing symptom development and disease severity [22]. In plants inoculated with the 'helper begomovirus' (DNA-A), in the absence of the DNAβ satellite, the virus accumulates to lower than wild type levels of virus accumulation, and symptoms are attenuated or entirely absent [19,22]. The only coding region known to occur on DNA β-satellites, is referred to as Beta C1 (βC1), which codes for a protein that functions as a suppressor of post-transcriptional gene silencing, and so is a key determinant of pathogenicity. Silencing of βC1 expression therefore is expected to interfere with the 'helper begomovirus' systemic infection of the host plant [19,22,23].

In an embodiment of the invention, a specific type of dsRNA, referred to as a small hairpin RNA (shRNA), was constructed, consisting of a cloned fragment of the AC1 gene Cotton leaf curl Kokhran virus-Burewala (CLCuKoV-Bu; HF567942), and a fragment of the βC1 coding region overlapping with the non-coding SCR of Cotton leaf curl Multan betasatellite (CLCuMB; HF567946). The sequence integrity of the fragments following sub-cloning was verified by confirmatory DNA sequencing, and the construct was transformed into *Gossypium hirsutum* "VH-289", a cotton variety that is adapted for cultivation in Pakistan.

2. Materials and Methods 2.1. Plasmid Construction for siRNA/Intron Spliced Hairpin RNA Generation An embodiment of the RNAi construct, an shRNA construct according to the invention, is schematically illustrated in FIG. 1. The RNAi construct, herein designated Vβ, was designed to target coding and non-coding regions of at least eight recognized "core" or "non-core" leaf curl disease causing viruses and associated betasatellites (sequence alignment) of cotton and some vegetable crop species, and any others that share sufficient sequence homology with the shRNA, such that viral gene silencing results. These targets were selected on the basis of their requirement for viral replication and satellite-mediated suppression of host-defenses and their reasonably high shared sequence. The hairpin construct was made by cloning a 720 bp fragment containing the target sequences in the plasmid vector pFGC5941 [5], in the sense and anti-sense orientations separated by a 1349 bp fragment of the chalcone synthase A coding region (ChsA), previously cloned from *Petunia X hybrida* Ailm [24]. The plasmid vector contains the constitutive 35S CaMV-promoter to drive expression in phloem and non-phloem tissues, and the octopine synthase (OCS) terminator.

The following sequence 1 illustrates the sense and anti-sense nucleotide sequences of an RNAi (shRNA) construct according to an embodiment of the invention.

The following is the sense target sequence (SEQ ID No. 1) of betasatellite and virus according to an embodiment. The virus portion is underlined, the restriction enzymes are shown in bold, and the remaining portion is the betasatellite sequence:

Xba1
TCTAGACCGGTTTTTGATAAAGGAGTGTATAGGTTTCACGAGAGATTGA

TTTCTTCTCCGTGAAAGGGTTAACGTTTGGGATCTTTGGGGCTGCTTCT

TCTTTAAGTAGTTCTAGACATCTCTCGAAGTGCTTCTACCCAGAGGCGT

ATAGGTACAAGAGTAGGTTAAGCTTCCCTTTAAGGTCACGTTTTTATTG

TCTAAGAAGCTGAACCAAAGGGGTTCAGCCAGTCGTGTAAAGGTAGGCT

TGTAAGTCCCCCGATTTA

EcoR1
GTCGCAGACTACAGTTTTTGATGTAGCGGTTTCTACCTCTGCAAGAATT

CACATGAACTTTTGGGTCTCTATAACCCTTACCTACATTAGCTTGGTAT

GTATAAGTTATTCTTCAAGTGTCAAATTTAAGGTTGGTGTTGGGTCATT

ACGTATAAATTGTGTGTATAGTGGTTGTTGTTTGTCTGGGTATTAGGTA

TTTGCCGGTAGAAGTTTCCGGGTTAGTGAAGGTTCAGGTAATTTAACCG

GGTAATCTTCAGTTTAGGTCAGTTCTGTTCGTCACCCTGGGTGACGCGC

CGGTAGCCCGTGGCGAGCGGGTGCCATTATAATCTTGCACCCGCTCGAT

TCGAGGCCGCATCGATTCCGACGACGCATCGCATCACCAAAGATGGGAG

GGTCCCCATGTGTGGCGGCGCGCATAGCATT

BamH1
TAACTACGGCCTTAGTCGGTCAAGGATCC

The following sequence 2 (SEQ ID No. 2) is the antisense target sequence of betasatellite and virus according to an embodiment of the invention. The virus portion is underlined, the restriction enzymes shown in bold, and the remaining portion is the betasatellite sequence:

Nco1
CCATGGAACTGGCTGATTCCGGCATCAATTTACGATACGCGCGGCGGTG

TGTACCCCTGGGAGGGTAGAAACCACTACGCTACGCAGCAGCCTTAGCT

ACGCCGGAGCTTAGCTCGCCCACGTTCTAATATTACCGTGGGCGAGCGG

TGCCCGATGGCCGCGCAGTGGGTCCCACTGCTTGTCTTGACTGGATTTG

ACTTCTAATGGGCCAATTTAATGGACTTGGAAGTGATTGGGCCTTTGAA

GATGGCCGTTTATGGATTATGGGTCTGTTTGTTGTTGGTGATATGTGTG

TTAAATATGCATTACTGGGTTGTGGTTGGAATTTAAACTGTGAACTTCT

TATTGAATATGTATGGTTCGATTAC

EcoR1
ATCCATTCCCAATATCTCTGGGTTTTCAAGTACAGAATTCAACGTCTCC

ATCTTTGGCGATGTAGTTTTTGACATCAGACGCTGATTTAGCCCCCTGA

ATGTTCGGATGGAAATGTGCTGACCGACTTGGGGAAACCAAGTCGAAGA

ATCTGTTATTTTTGCACTGGAATTTCCCTTCGAATTGGATGAGAACATG

GATATGCGGAGACCCATCTTCGTGAAGCTCTCTACAGATCTTGATGAAT

TTCTTCTTCGTCGGGGTTTCTAGGGTTTGCAATTGGGAAAGTGCCTCTT

CTTTAGTTAGAGAGCACTTTGGA

Xho1
TATGTGAGGAAATAGTTTTTGGCCCTCGAG

2.2. Cotton Plant Transformation

Seeds of the cotton variety "VH-289" were obtained from the Central Cotton Research Institute (CCRI, Multan, Pakistan). However, the construct and methods of the present invention may also be used in other varieties of cotton plants.

The delinted seeds were held in high moisture conditions for germination, and plant transformation was carried out, as previously described [25] and as incorporated herein by reference. In addition, some non-transformed embryos were plated on MS medium to create a transformation-minus control. The putative, transgenic cotton plants were selected using Basta herbicide also known as glufosinate-ammonium a broad-spectrum systemic herbicide (Bayer Crop Science, Thane, Maharashtra, India) at 200 mg/L, for two-months, and the non-transgenic plants were cultured on rooting and shooting medium, with and without Basta selection. The plantlets surviving herbicide selection, and non-transgenic control plantlets which survived on medium without Basta selection, were transferred to pots containing a potting mix, and acclimatized to greenhouse conditions. The seeds were collected from positively transformed plants, confirmed by PCR amplification and sequencing of amplicons, planted, and grown under controlled conditions to produce the $T_1$ generation seed.

2.3. Molecular Analysis of Transgenic Cotton Plants

Total DNA was purified from the emerging leaves of transgenic and non-transgenic plants using the CTAB (cetyl trimethylammonium bromide) method [26]. Positively transformed plants were identified by PCR amplification of a fragment of CLCuKoV-Bur AC1 using the specific primers, F-5'-TGCCAAAAACTATTTCCTCACAT-3' (SEQ ID NO. 3) and R-5'-AACGTCTCCATCTTTGGCG-3' (SEQ ID NO. 4), to obtain an expected size product of 301 bp, as described previously [27].

2.4. Challenge-Inoculation of Transgenic Plants

Resistance to CLCuD in $T_0$ and $T_1$ (generations 0 and 1) transgenic cotton plants was evaluated on the basis of symptom development, and disease severity rating score, as described previously [28] and is incorporated herein by reference. Adult whiteflies, *B. tabaci* (Asia II major clade mitotype), were allowed a four-day acquisition access period (AAP) on cotton plants infected with CLCuKoV-Bur and CLCuMB and transferred to 4-6 leaf stage transgenic and non-transgenic cotton seedlings, at the 3-4 leaf stage, for a four-day inoculation access period (TAP). Whiteflies were killed by insecticide treatment. Plants were maintained an insect-free greenhouse, and observed periodically for symptom development, and observations were recorded, three weeks post-inoculation.

2.5. Real-Time Polymerase Chain Reaction Analysis

Figure 7A:
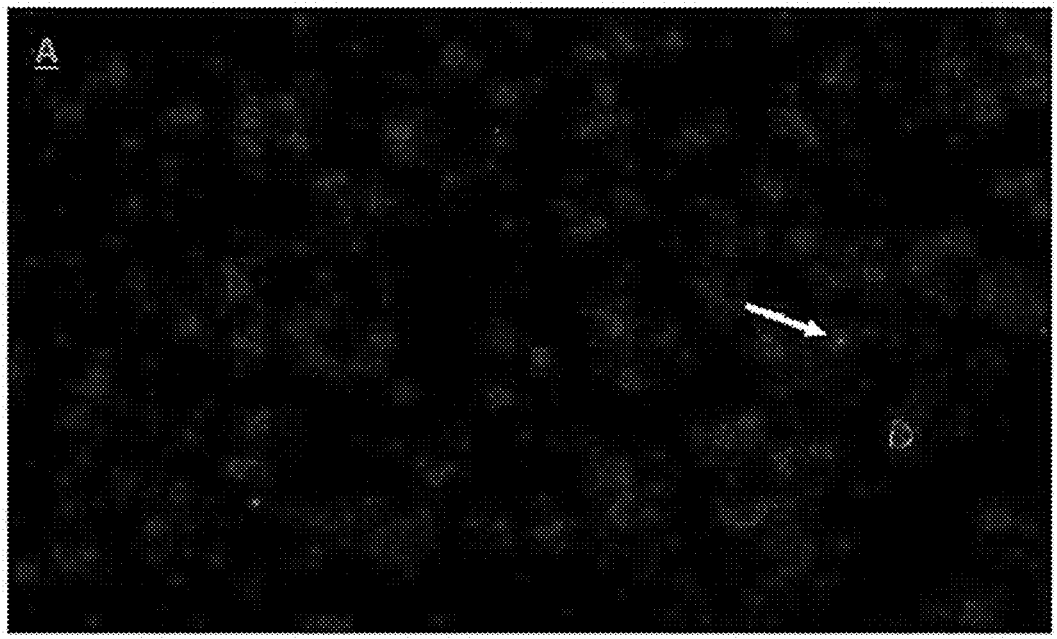
FIGS. 7A and 7B illustrate the results of fluorescence in situ hybridization (FISH) of a small hairpin RNA (shRNA) construct (also referred to herein as a dsRNA hairpin construct or a VP construct) in $T_1$ generation plants.
Figure 7B:
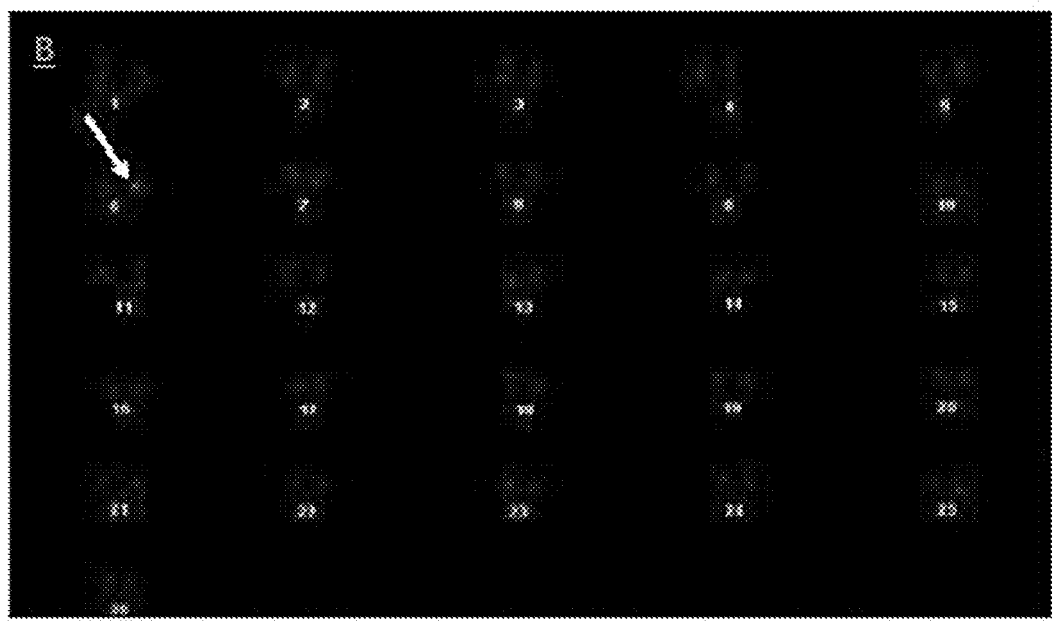

Virus accumulation in virus-inoculated, transgenic cotton plants harboring the shRNA hairpin construct designed to silence expression of begomovirus-beta satellite gene and non-coding region sequences targeted by RNAi, was quantified using the Thermo Scientific Maxima SYBR Green qPCR kit (cat# K0241) (Thermo Fisher Scientific, Waltham, Mass., United States of America). Total DNA was isolated from cotton plants, diluted 10-fold, and used as a template for quantitative, real-time PCR amplification. A cloned, full-length CLCuMB molecule was used as the baseline reference sequence for quantification. Total DNA isolated from a cotton plant infected with CLCuKoV-Bur/CLCuMB, or from a virus-free plant and included as positive and negative experimental controls, respectively. Cycling conditions were: 5 min at 95° C. for 40 cycles, 30 s at 95° C., and 30 s at 55° C. The melting curve was produced by denaturing the amplicon in a temperature gradient of 60 to 95° C. to confirm specificity of the CLCuMB primers, βF-5-AGTGCGCTGAAAAAGGTGAT-3' (SEQ ID NO. 5) and βR-5-ATTAAAACGTGAAAAAGGTGAT-3' (SEQ ID NO. 6). The fold-change was calculated by comparing the normalized transcript levels reflecting viral-betasatellite gene expression in transgenic plants, results obtained for DNA from control plants.

2.6. Fluorescence In Situ Hybridization

Using the Fluorescein ULS® Labeling Kit Cat. No. K0641 (Fermentas-Thermoscience Fisher, Waltham, Mass., USA), the probe for transgene detection was labeled according to the manufacturer's instructions. In situ hybridization was performed, as previously described [29], and is incorporated herein by reference thereto, for metaphase chromosomal spreads [12], with the counterstaining of hybridized slides, copy number determination, and transgene localization on cotton chromosomes, as previously described [9,29, 30], and is incorporated herein by reference thereto.

2.7. In Silico Analysis of dsRNA Hairpin Structure

The complete sequences of viral AC1 and βC1 genes, and a non-coding region found in CLCuKoV-Bu and CLCuMB will be targeted using RNAi. The sense and anti-sense sequences for each of the target regions used to build the shRNA construct according to an embodiment of the invention were obtained by PCR amplification of the virus-betasatellite complex, cloned into the plasmid vector pFGC5941, and subjected to confirmatory sequencing. The "spacer", or the sequence used to achieve loop formation, was a previously engineered fragment of the ChsA gene that we inserted during construction/cloning between the selected sense/anti-sense target sequences.

The DNA sequences were converted to RNA using the Sequence Conversion tool [31] available at In-silico.net. The RNA sequences were analyzed using the on-line RNA secondary structure prediction tool, RNA structure [32] available at Predict a Secondary Structure Web Server [33].

3. Results 3.1. Genetic Transformation of Cotton

Transformation of the cotton variety "VH-289" with the VP construct was done using the embryo shoot apex cut method, as previously described [14], and is incorporated herein by reference. Two days post co-cultivation the cotton plantlets were transferred to selection media, containing 200 mg/L Basta (Bayer Crop Science Thane, Maharashtra, India) for positive selection screening, with the addition of phytohormone indole-3-butyric acid (IBA) (0.1 mg/L) to facilitate root establishment. The efficiency of transformation was 2.8% (TABLE 1). After the plants were acclimatized to greenhouse conditions, leaf samples were collected from cotton plants, and used for molecular analysis and karyotyping.

TABLE 1

Efficiency of Cotton Plant Transformation with the Vβ construct.

| Experiment Number | Seeds (n) | Embryos (n) | Embryos Transferred to MS Media (n) | Embryos Transferred to Glass Tube (n) | Plants Transferred to Greenhouse (n) | Plants in the Field (n) |
|---|---|---|---|---|---|---|
| 1 | 20 g | 10 | 10 | 0 | 0 | 0 |
| 2 | 20 g | 30 | 28 | 28 | 5 | 1 |
| 3 | 20 g | 45 | 38 | 20 | 6 | 1 |
| 4 | 20 g | 70 | 70 | 12 | 1 | 0 |
| 5 | 40 g | 100 | 95 | 15 | 8 | 3 |
| 6 | 20 g | 35 | 30 | 0 | 0 | 0 |
| 7 | 40 g | 132 | 132 | 10 | 7 | 4 |
| 8 | 20 g | 10 | 10 | 10 | 2 | 1 |
| 9 | 20 g | 33 | 33 | 14 | 5 | 3 |
| Total | 220 g | 465 | 465 | 109 | 34 | 13 |

3.2. Confirmation of Transgene Presence in $T_0$ and $T_1$ Plants

Confirmatory PCR amplification using viral AC1-specific primers was carried out to confirm transformation of the 11 resultant cotton plants. The expected size ~300 bp fragment, corresponding to a region of AC1, was amplified from the nine $T_0$ cotton plants that survived acclimatization. Seven of the $T_1$ transgenic cotton plants were positive, based on PCR amplification, which yielded the expected size band of ~300 bp, cloning, and confirmatory DNA sequencing, as illustrated in FIGS. 2A and 2B.

3.3. Challenge Inoculation of Transgenic Plants with Wild Type Begomovirus-Betasatellite Viruses by Whitefly Vector Mediated Inoculation Challenge-inoculation study was carried out using adult, viruliferous whiteflies (10+ per plant) to inoculate the greenhouse-maintained transgenic and non-transgenic (negative control) cotton plants with CLCuKoV-Bu/CLCuMB. Characteristic CLCuKoV-Bu/CLCuMB symptoms developed in all of the non-transgenic plants (TABLE 2), three weeks post-inoculation. However, leaf curl symptoms were not observed in the transgenic $T_0$ and $T_1$ cotton plants, with one exception, line T1Vβ4 ($T_1$), which exhibited mild leaf curl symptoms, receiving a symptom severity score of 1. A symptom severity index was implemented to assign a disease severity score to each test plant. The severity index score virus-infected, non-transgenic, positive control plants was 83.3%, whereas, the $T_0$ and $T_1$ transgenic plant scores were 0% and 4.16%, respectively. Seed was further increased to produce the T2 and then T3 generations. Additional challenge-inoculation experiments are underway with T3 generations with multiple, naturally-occurring wild type virus-betasatellite species and strains, with subsequent molecular analyses.

six $T_1$ transgenic cotton plants. The transgene for a selected plant of line Vβ6 that was asymptomatic and had the lowest relative virus accumulation among $T_1$ generation plants was localized to chromosome 6. The results of the FISH and karyotyping analyses are illustrated in FIGS. 7A and 7B.

3.6. Bioinformatic Analysis of the RNAi Construct

Figure 8:
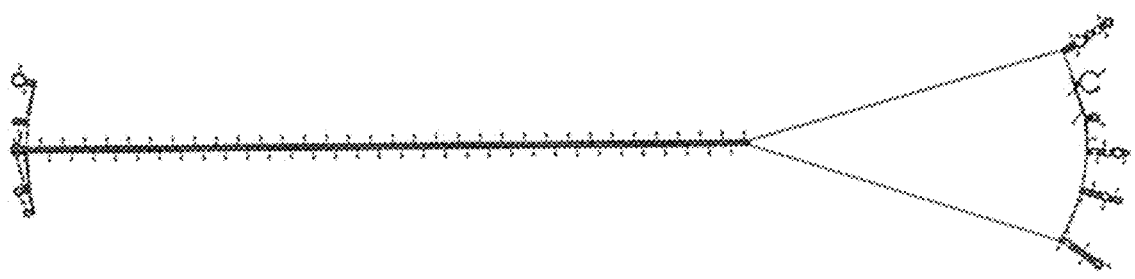
FIG. 8 is a representation of the RNA secondary structure of the VP construct, as predicted by the RNA structure tool.

Analysis of the shRNA hairpin region of the construct according to an embodiment of the invention using an RNA structure prediction tool [32], indicated the secondary structure of the molecule contained the loop and long, double-stranded RNA structure optimal for effective RNA-interference activity. The accuracy of prediction was determined to be 90%. FIG. 8 is a representation of the RNA secondary structure of a VP construct according to the invention, as predicted by the RNA structure tool.

TABLE 2

Comparison of disease severity scores [1] for CLCuKoV-Bu-CLCuMB-inoculated $T_0$ (generation 0) and $T_1$ (generation 1) transformed and non-transformed cotton plants.

| Control | C-1 | C-2 | C-3 | C-4 | C-5 | C-6 | C-7 | C-8 | C-9 |
|---|---|---|---|---|---|---|---|---|---|
|  | 6 | 6 | 4 | 4 | 4 | 5 | 5 | 6 | 5 |
| $T_0$ | Vβ1 | Vβ2 | Vβ3 | Vβ4 | Vβ5 | Vβ6 | Vβ7 | Vβ8 | Vβ9 |
|  | 0 | 0 | 0 | 0 | 0 | 0 | 0 | 0 | 0 |
| Control | C1-1 | C2-1 | C4-1 | C6-1 |  |  |  |  |  |
|  | 5 | 5 | 5 | 5 |  |  |  |  |  |
| $T_1$ | $T_1$Vβ1 | $T_1$Vβ2 | $T_1$Vβ4 | $T_1$Vβ6 |  |  |  |  |  |
|  | 0 | 0 | 1 | 0 |  |  |  |  |  |

In TABLE 2, the rating system is: 0=no symptoms, 1-5=incrementally, increasingly severe, and 6=characteristic, severe leaf curl symptoms caused by Cotton leaf curl Kokhran virus-Burewala/Cotton leaf curl Multan betasatellite (CLuKoV-Bu/CLCuMB) infection of susceptible cultivars.

Figure 3:
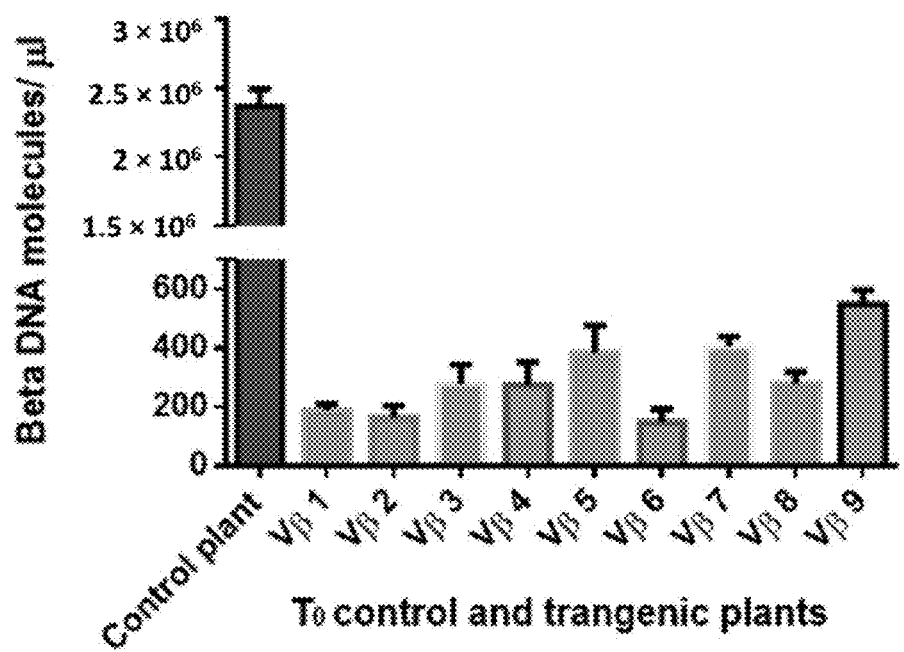
FIG. 3 illustrates results of quantitative PCR amplification detection of CLCuMB molecules/μL in total DNA purified from the nine $T_0$ transgenic cotton plants (Vβ1-Vβ9), compared to a non-transgenic, positive control cotton plant.
Figure 4:
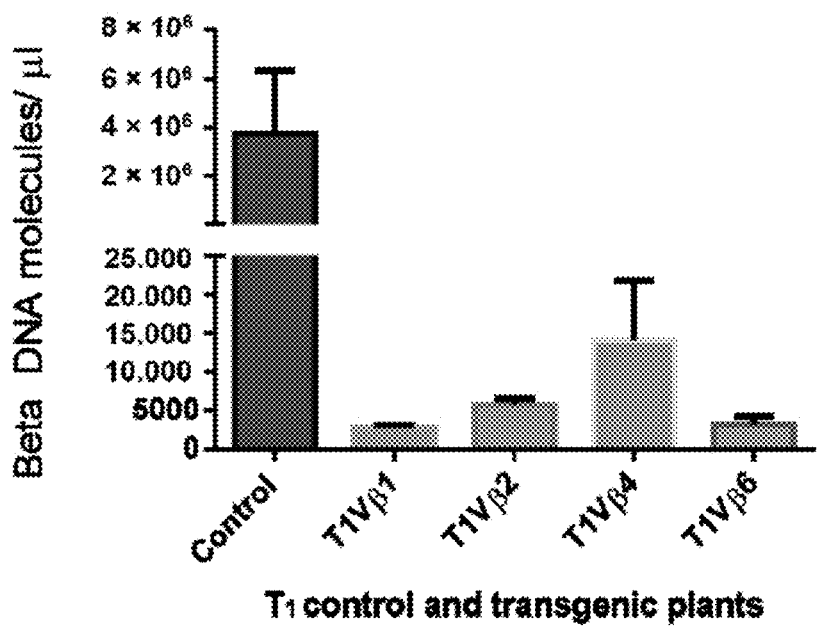
FIG. 4 illustrates results of quantitative PCR amplification detection of CLCuMB molecules/μL in total DNA purified from the $T_1$ transgenic cotton plants, T1Vβ1, T1Vβ2, T1Vβ4, T1Vβ6, compared to a non-transgenic, positive control cotton plant.
Figure 5:
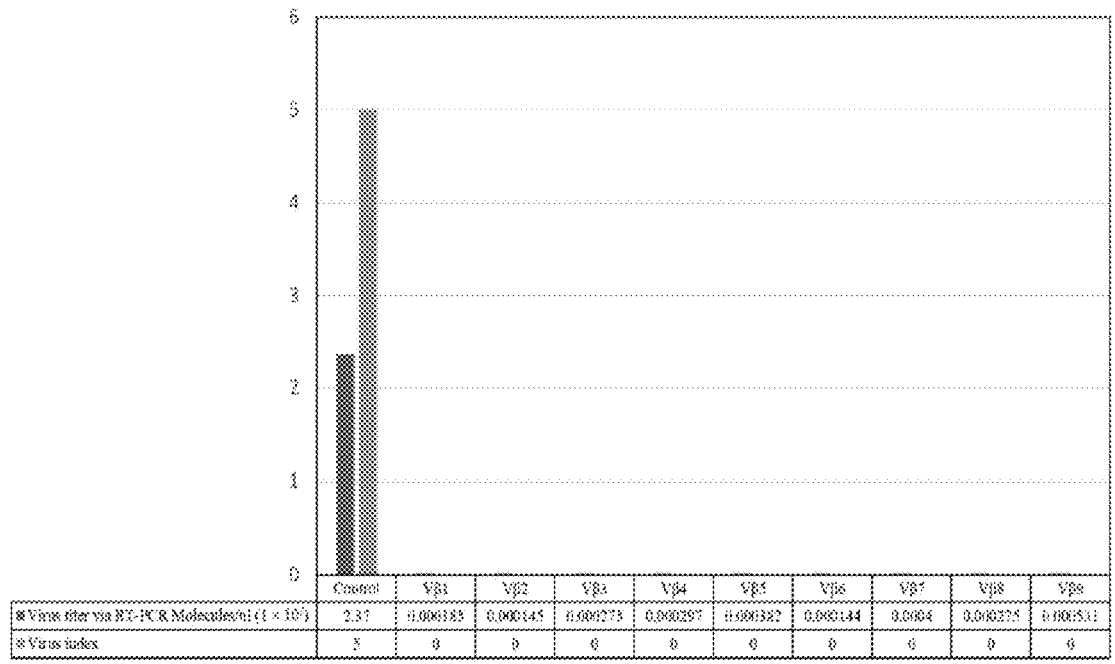
FIG. 5 illustrates a comparison of virus disease severity score with virus accumulation in the $T_0$ transgenic cotton plants, lines Vβ1-Vβ9, and a non-transgenic, positive control cotton plant.
Figure 6:
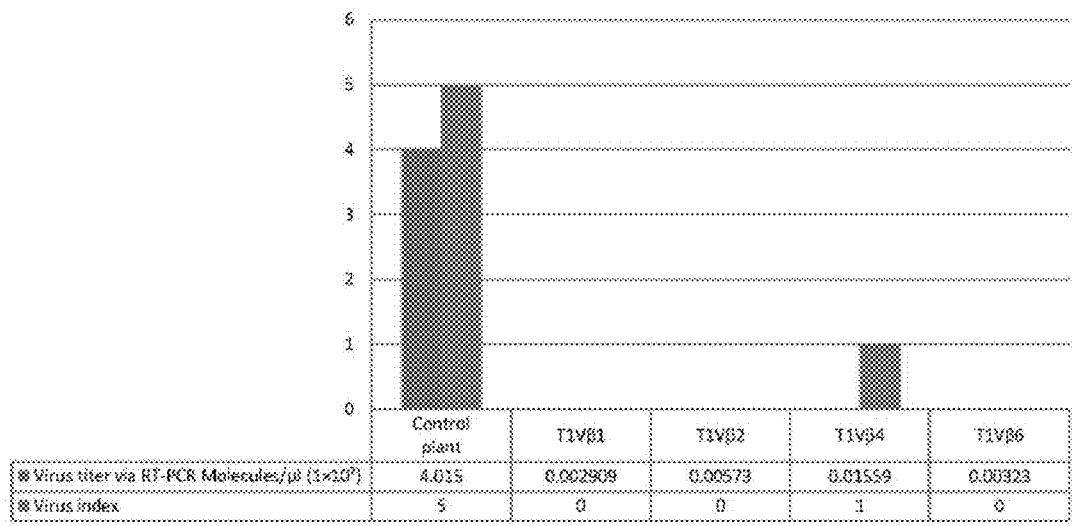
FIG. 6 illustrates a comparison of disease severity score and virus accumulation in the $T_1$ transgenic cotton plants, lines T1Vβ1, T1Vβ2, T1Vβ4, T1Vβ6, and a non-transgenic, control cotton plant.

3.4. Betasatellite Accumulation in Transgenic and Non-Transgenic Cotton Plants, Post-Virus Inoculation Using Viruliferous Whiteflies Virus accumulation in transgenic and non-transgenic (susceptible), positive control plants was quantified by real-time PCR amplification, using primers specific to the DNA β-satellite CLCuMB, corresponding to a region not used for transgene construction. Betasatellite accumulation was negligible in the asymptomatic transgenic cotton plants, at 180-600 and 2500-15,590 molecules/µL for the $T_0$ and $T_1$ plants, compared to the symptomatic, non-transgenic, positive control plants, in which 4,015,249 CLCuMB molecules/µL were detected. Thus, the transgenic $T_0$ and $T_1$ generation plants, which exhibited no evidence of leaf curl symptoms post-virus inoculation, accumulated significantly less CLCuMB than symptomatic, non-transgenic control cotton plants included as the positive experimental controls, e.g., the positive experimental controls were susceptible to begomovirus infection. In this regard, see FIGS. 3 and 4, which further illustrate the beneficial effects of cotton plants transformed with the shRNA construct according to an embodiment of the invention. Also, for the $T_0$ and $T_1$ transgenic plant generations, the severity of disease symptoms, virus accumulation, and disease severity rating were positively correlated, as illustrated in FIGS. 5 and 6.

3.5. Fluorescence In Situ Hybridization Analysis

Integration and chromosome location in cotton plants of the shRNA (hairpin) construct according to an embodiment of the invention was confirmed by fluorescence in situ hybridization (FISH) and karyotyping, respectively. The presence of a single copy of the transgene was confirmed in 4. Discussion In this study, the cotton variety "VH-289", which is adapted to Pakistan growing conditions, was transformed with a dsRNA, anti-viral hairpin construct, referred to herein, as shRNA or Vβ. The aim was to knock down or reduce the expression of the CLCuKoV-Bu AV1 gene and a nearby non-coding viral sequence essential for viral replication initiation, and of the βC1 gene and SCR region of CLCuMB, using the *Agrobacterium*-mediated embryo shoot apex cut method, as previously described [25, 27]. The transgenic cotton plants harboring the Vβ construct showed substantially reduce betasatellite accumulation. The presence of the transgene construct was verified for cotton lines of the $T_0$ and the $T_1$ generations by PCR amplification of a ~300 bp fragment of the CLCuKoV AC1 gene, which is essential for the initiation of begomoviral and betasatellite replication. FISH analysis and karyotyping of the Vβ6 plant, which was asymptomatic and had the lowest virus accumulation among the $T_1$ generation plants, indicated the transgene was inserted as a single copy on chromosome 6. In contrast, *Agrobacterium*-mediated transformation can result in random integration of multiple transgene(s) of variable copy number [30].

Here, two successive generations (now $T_3$) of transgenic cotton plants were developed and evaluated for resistance to CLCuKoV-Bu and CLCuMB infection. Evidence for effective begomoviral-satellite knockdown ($T_0$, $T_1$) was provided following challenge-inoculation of plants by viruliferous whiteflies, which resulted in the development of characteristic leaf curl symptoms in non-transgenic, positive control cotton plants, and absence of symptom development for all but one of the transgenic plant lines tested.

Quantitative PCR analysis of the virus challenge-inoculated cotton plants indicated greatly reduced accumulation of the DNA β-satellite, CLCuMB, in the Vβ transgenic $T_0$ and $T_1$ generation plants, compared to non-transgenic cotton plants. For the non-transgenic susceptible and wild type virus-inoculated "control" plants, 2,367,884 molecules/µL and 4,015,249 molecules/µL of CLCuMB were detected, compared to extremely low levels for the $T_0$ and $T_1$ generation plants at 600 and 15,590 molecules/µL, respectively. See FIGS. 3 and 4 for graphical representation of the results of this PCR analysis. Finally, a positive correlation was observed between virus accumulation and disease severity in $T_0$ and $T_1$ generation plants. In this regard, see FIGS. 5 and 6. Asad et al. [10] showed some extent of protection by expressing siRNA sequences homologous to the viral AC1, AC2 and AC3 coding regions expressed in transgenic tobacco plants, in that challenge-inoculated plants showed ameliorated foliar symptoms. Another group demonstrated some level of leaf curl resistance in transgenic cotton G. hirsutum "Coker 310" plants expressing an antisense βC1, which exhibited reduced symptom severity [13]. Using the cotton leaf curl disease severity rating system of Akhtar and Khan 2002 [34], scores of 4 to 6 were assigned to non-transgenic cotton plants showing severe leaf curling, vein-thickening, enations, and stunting of plants, while transgenic plants were scored as 0 to 1, and developed mild or no symptoms. Thus, these results are also consistent with those of a previous study [35] that reported a positive relationship between begomovirus accumulation and symptom severity.

The durability of transgenic resistance mediated by RNAi for the simultaneous knock down of begomoviral and betasatellite expression, will continue to be evaluated by subjecting plants to infection by different "core" and "non-core" strains and species of the leaf curl complex, including any closely-related leaf curl species that may share sequence homology in the viral and betasatellite regions targeted by this transgene construct. It may well protect against multiple different viral and betasatellite species and strains, even in the absence of 100% shared sequence homology with the shRNA construct. It is well known that betasatellites are promiscuous with respect to compatibility with multiple leaf curl strains and species, and so at the very least, this construct should act as a suppressor of host-mediated post-transcriptional silencing accordance with a well-known wild type function [19]. Nonetheless, the sequence-specific nature of RNAi would strongly suggest that these transgenic cotton plants can provide protection against multiple species and strain affiliates of the cotton leaf curl virus disease complex from south Asia, and additional begomoviral species or strains (and betasatellites), prevalent now or in the future, infecting cotton in Pakistan.

REFERENCES

The following References and all that they each disclose are incorporated into this patent application by reference hereto. Throughout the specification, the following References are referred to by their respective number within brackets.

1. Briddon, R. W.; Markham, P. Cotton leaf curl virus disease. *Virus Res.* 2000, 71, 151-159.
2. Farooq, A.; Farooq, J.; Mahmood, A.; Shakeel, A.; Rehman, A.; Batool, A.; Riaz, M.; Shahid, M.; Mehboob, S. An overview of cotton leaf curl virus disease (CLCuD) a serious threat to cotton productivity. *Aust. J. Crop Sci.* 2011, 5, 1823-1831.
3. Farooq, J.; Farooq, A.; Riaz, M.; Shahid, M. R.; Saeed, F.; Iqbal, M. S.; Hussain, T.; Batool, A.; Mahmood, A. Cotton leaf curl virus disease a principle cause of decline in cotton productivity in Pakistan (a mini review). *Can. J. Plant Prot.* 2014, 2, 9-16.
4. Ali, A.; Abdulai, A. The Adoption of Genetically Modified Cotton and Poverty Reduction in Pakistan. *J. Agric. Econ.* 2010, 61, 175-192.
5. Kerschen, A.; Napoli, C. A.; Jorgensen, R. A.; Müller, A. E. Effectiveness of RNA interference in transgenic plants. *FEBS Lett.* 2004, 566, 223-228.
6. Kirthi, N.; Savithri, H. S. A conserved zinc finger motif in the coat protein of Tomato leaf curl Bangalore virus is responsible for binding to ssDNA. *Arch. Virol.* 2003, 148, 2369-2380.
7. Klahre, U.; Crete, P.; Leuenberger, S. A.; Iglesias, V. A.; Meins Jr., F. High molecular weight RNAs and small interfering RNAs induce systemic posttranscriptional gene silencing in plants. *Proc. Natl. Acad. Sci. USA* 2002, 99, 11981-11986, doi:10.1073/pnas.182204199.
8. Hannon, G. J. RNA interference. *Nature* 2002, 418, 244-251.
9. Aragão, F. J.; Faria, J. C. First transgenic geminivirus-resistant plant in the field. *Nat. Biotechnol.* 2009, 27, 1086-1088.
10. Asad, S.; Haris, W. A. A.; Bashir, A.; Zafar, Y.; Malik, K. A.; Malik, N. N.; Lichtenstein, C. P. Transgenic tobacco expressing geminiviral RNAs are resistant to the serious viral pathogen causing cotton leaf curl disease. *Arch. Virol.* 2003, 148, 2341-2352.
11. Baulcombe, D. RNA silencing. *Trends Biochem. Sci.* 2005, 30, 290-293.
12. Shepherd, D. N.; Martin, D. P.; Thomson, J. A. Transgenic strategies for developing crops resistant to geminiviruses. *Plant Sci.* 2009, 176, 1-11.
13. Sohrab, S. S.; Kamal, M. A.; Ilah, A.; Husen, A.; Bhattacharya, P. S.; Rana, D. Development of Cotton leaf curl virus resistant transgenic cotton using antisense βC1 gene. *Saudi J. Biol. Sci.* 2014, 23, 358-362.
14. Muzaffar, A.; Kiani, S.; Khan, M. A. U.; Rao, A. Q.; Ali, A.; Awan, M. F.; Iqbal, A.; Nasir, I. A.; Shahid, A. A.; Husnain, T. Chloroplast localization of Cry1Ac and Cry2A protein-an alternative way of insect control in cotton. *Biol. Res.* 2015, 48, 14.
15. Malik, H. J.; Raza; A; Amin, I.; Scheffler, J. A.; Scheffler, B. E.; Brown, J. K.; Mansoor, S. RNAi-mediated mortality of the whitefly through transgenic expression of double stranded RNA homologous to acetylcholinesterase and ecdysone receptor in tobacco plants. *Sci. Rep.* 2016, 6, 38469.
16. Vyas, M.; Raza, A.; Ali, M. Y.; Ashraf, M. A.; Mansoor, S.; Ahmad, A. S.; Brown, J. K. Knock down of Whitefly Gut Gene Expression and Mortality by Orally Delivered Gut Gene-Specific dsRNA. *PLoS ONE* 2017, 12, e0168921, doi:10.1371/journal.pone.016892.
17. Amin, I.; Hussain, K.; Akbergenov, R.; Yadav, J. S.; Qazi, J.; Mansoor, S.; Hohn T.; Fauquet, C. M., Briddon, R. W. Suppressors of RNA Silencing Encoded by the Components of the Cotton Leaf Curl Begomovirus-BetaSatellite Complex. *Mol. Plant Microbe Interact.* 2011, 24, 973-983.
18. Briddon, R. W.; Stanley, J. Subviral agents associated with plant single-stranded DNA viruses. *Virology* 2006, 344, 198-210.
19. Cui, X.; Li, G.; Wang, D.; Hu, D.; Zhou, X. A Begomovirus DNAβ-Encoded Protein Binds DNA, Functions as Suppressor of RNA Silencing, and Targets the Cell Nucleus. *J. Virol.* 2005, 79, 10764-10775.
20. Kong, L. J.; Orozco, B. M.; Roe, J. L.; Nagar, S.; Ou, S.; Feiler, H. S.; Durfee, T.; Miller, A. B.; Gruissem, W.; Robertson, D.; Hanley-Bowdoin, L. A geminivirus replication protein interacts with the retinoblastoma protein through a novel domain to determine symptoms and tissue specificity of infection in plants. *J. EMBO.* 2000, 19, 3485-3495.
21. Laufs, J.; Schumacher, S.; Geisler, N.; Jupin, I.; Gronenborn, B. Identification of the nicking tyrosine of geminivirus Rep protein. *FEBS Lett.* 1995, 377, 258-262.
22. Saeed, M.; Behjatnia, S. A. A.; Mansoor, S.; Zafar, Y.; Hasnain, S.; Rezaian, M. A. A Single Complementary-Sense Transcript of a Geminiviral DNA 13 Satellite Is Determinant of Pathogenicity. *Mol. Plant Microbe Interact.* 2005, 18, 7-14.
23. Saeed, M.; Zafar, Y.; Randles J, W.; Rezaian, M. A. A monopartite begomovirus-associated DNA β satellite substitutes for the DNA B of a bipartite begomovirus to permit systemic infection. *J. Gen. Virol.* 2007, 88, 2881-2889.
24. Napoli, C.; Lemieux, C.; Jorgensen, R. Introduction of a Chimeric Chalcone Synthase Gene into *Petunia* Results in Reversible Co-Suppression of Homologous Genes in trans. *Plant Cell* 1900, 2, 279-289.
25. Rao, A. Q.; Bakhsh, A.; Kiani, S.; Shahzad, K.; Shahid, A. A.; Husnain, T.; Riazuddin, S. The myth of plant transformation. *Biotechnol. Adv.* 2009, 27, 753-763.
26. Doyle, J. J.; Doyle, J. L. A rapid DNA isolation procedure for small quantities of fresh leaf tissue. *Phytochem. Bull.* 1987, 19, 11-15.
27. Rao, A. Q.; Irfan, M.; Saleem, Z.; Nasir, I. A., Riazuddin, S.; Husnain, T. Overexpression of the phytochrome B gene from *Arabidopsis thaliana* increases plant growth and yield of cotton (*Gossypium hirsutum*). *J. Zhejiang Univ. Sci. B* 2011, 12, 326-334.
28. Akhtar, K. P.; Ullah, R.; Khan, I. A.; Saeed, M.; Sarwar, N.; Mansoor, S. First Symptomatic Evidence of Infection of *Gossypium arboreum* with Cotton Leaf Curl Burewala Virus Through Grafting infection of *Gossypium arboreum* with Cotton leaf curl Burewala virus through grafting. *Int. J. Agric. Biol.* 2013, 15, 157-160.
29. Rahman, M.; Noreen, S.; Husnain, T.; Riazuddin, S. A fast and efficient method to determine the position of alien genes in transgenic plants. *Emir. J. Food Agric.* 2010, 22, 223-231.
30. Rahman, N.; Khatoon, A.; Rahman, H. Studies on the development of spectrophotometric method for the determination of haloperidol in pharmaceutical preparations. *Quim. Nova* 2012, 35, 392-397.
31. In-silico Project support for life sciences (January 2016) http://in-silico.net/tools/biology/sequence conversion
32. Mathews, D. H.; Turner, D. H.; Watson, R. M. RNA Secondary Structure Prediction. *Curr. Protoc. Nucleic Acid Chem.* 2007, Chapter 11, Unit 11.2.
33. Predict a Secondary Structure Web Server (January 2016) http://rna.urmc.rochester.edu/RNAstructureWeb/Servers/Predict1/Predict1.html.
34. Akhtar, K. P.; Khan, A. I.; Hussain, M.; Khan, M. S. I. Comparison of Resistance Level to Cotton leaf curl virus (CLCuV) Among Newly Developed Cotton Mutants and Commercial Cultivars. *J. Plant Pathol.* 2002, 18, 179-186.
35. Ammara, U.; Mansoor, S.; Saeed, M.; Amin, I.; Briddon, R.; Al-Sadi, A. RNA interference-based resistance in transgenic tomato plants against Tomato yellow leaf curl virus-Oman (TYLCV-OM) and its associated betasatellite. *J. Virol.* 2015, 12, 38.

What is claimed is:

1. A nucleic acid construct encoding an RNA sequence that forms a hairpin when expressed, said RNA sequence comprising a sense sequence complementary to a portion of SEQ ID NO:1 that simultaneously targets an AC1 gene and associate betasatellite BC1 gene of a begomovirus, wherein expression of the construct in a plant infected with the begomovirus causes a reduction in expression of the AC1 and BC1 genes.

2. The nucleic acid construct of claim 1 further comprising: an antisense fragment complementary to a portion of SEQ ID. No. 2.

3. The nucleic acid construct of claim 2, further comprising:

(a) a promoter functional in a cotton plant; and (b) a terminator functional in the plant.

4. An *Agrobacterium* plasmid vector containing the nucleic acid construct of claim 1 for transforming a cotton plant.

* * * * *